(12) United States Patent
Yamamoto (10) Patent No.: US 10,729,331 B2
(45) Date of Patent: Aug. 4, 2020

(54) PHOTOACOUSTIC IMAGE GENERATION METHOD AND APPARATUS

(71) Applicant: FUJIFILM Corporation, Tokyo (JP)

(72) Inventor: Hiroaki Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 543 days.

(21) Appl. No.: 15/459,301

(22) Filed: Mar. 15, 2017

(65) Prior Publication Data

US 2017/0181640 A1 Jun. 29, 2017

Related U.S. Application Data

(63) Continuation of application No. PCT/JP2015/004392, filed on Aug. 31, 2015.

(30) Foreign Application Priority Data

Sep. 19, 2014 (JP) ................................ 2014-191561

(51) Int. Cl.
*A61B 5/00* (2006.01)
*A61B 8/08* (2006.01)
(Continued)

(52) U.S. Cl.
CPC .......... *A61B 5/0095* (2013.01); *A61B 8/0841* (2013.01); *A61B 8/14* (2013.01); *A61B 8/5207* (2013.01); *A61B 2017/3413* (2013.01)

(58) Field of Classification Search
CPC .......... A61B 2017/3413; A61B 5/0095; A61B 8/0841; A61B 8/14; A61B 8/5207
See application file for complete search history.

(56) References Cited

U.S. PATENT DOCUMENTS

2005/0004458 A1 1/2005 Kanayama et al.
2012/0253180 A1 10/2012 Emelianov et al.
(Continued)

FOREIGN PATENT DOCUMENTS

JP 2005-021380 A 1/2005
JP 2005-342128 A 12/2005
(Continued)

OTHER PUBLICATIONS

Extended European Search Report, dated Sep. 6, 2017, for European Application No. 15841830.1.
(Continued)

*Primary Examiner* — Michael T Rozanski
(74) *Attorney, Agent, or Firm* — Birch, Stewart, Kolasch & Birch, LLP (57) ABSTRACT

In a photoacoustic image generation apparatus for generating a photoacoustic image of a subject including an interventional instrument for each scanning plane, there are provided: means for generating a reflected acoustic wave image of the subject for each scanning plane; means for detecting a change in a photoacoustic image on an observation scanning plane, which is generated as an image, from a plurality of photoacoustic images regarding the observation scanning plane; means for detecting a change in a reflected acoustic wave image on the observation scanning plane from a plurality of reflected acoustic wave images regarding the observation scanning plane; determination means for determining whether or not a distal end of the interventional instrument is present on the observation scanning plane based on the change in the photoacoustic image and the change in the reflected acoustic wave image; and notification means for sending notification of a result of the determination.

10 Claims, 5 Drawing Sheets

(51) Int. Cl.
  *A61B 8/14*  (2006.01)
  *A61B 17/34*  (2006.01)

(56) References Cited

U.S. PATENT DOCUMENTS

| | | |
|---|---|---|
| 2012/0296192 A1 | 11/2012 | Fukutani |
| 2013/0218024 A1 | 8/2013 | Boctor et al. |
| 2015/0297092 A1 | 10/2015 | Irisawa |

FOREIGN PATENT DOCUMENTS

| | | |
|---|---|---|
| JP | 2006-055407 A | 3/2006 |
| JP | 2011-217767 A | 11/2011 |
| JP | 2013-013713 A | 1/2013 |
| JP | 2013-027513 A | 2/2013 |
| WO | WO 2014/109148 A1 | 7/2014 |

OTHER PUBLICATIONS

Chinese Office Action and Search Report dated Mar. 6, 2019, for Chinese Patent Application No. 201580048582.3, with English translation of the Chinese Office Action.

Su et al., "Photoacoustic Imaging of Clinical Metal Needles in Tissue", Journal of Biomedical Optics, vol. 15, No. 2, Mar./Apr. 2010, pp. 021309-1 to 021309-6.

International Search Report (PCT/ISA/210) issued in PCT/JP2015/004392, dated Dec. 22, 2015.

Written Opinion (PCT/ISA/237) issued in PCT/JP2015/004392, dated Dec. 22, 2015.

PHOTOACOUSTIC IMAGE GENERATION METHOD AND APPARATUS

CROSS-REFERENCE TO RELATED APPLICATIONS

This application is a Continuation of PCT International Application No. PCT/JP2015/004392 filed on Aug. 31, 2015, which claims priority under 35 U.S.C. § 119(a) to Japanese Patent Application No. 2014-191561 filed on Sep. 19, 2014. Each of the above applications is hereby expressly incorporated by reference, in its entirety, into the present application.

BACKGROUND OF THE INVENTION

1. Field of the Invention

The present invention relates to a photoacoustic image generation method, that is, a method of emitting light toward a subject and imaging the subject based on acoustic waves generated from a part of the subject that has received the light.

In addition, the present invention relates to an apparatus for implementing such a photoacoustic image generation method.

2. Description of the Related Art

As conventionally disclosed in, for example, JP2005-021380A and JP2011-217767A, a photoacoustic imaging apparatus for imaging the inside of a living body using the photoacoustic effect has been known. In this photoacoustic imaging apparatus, pulsed light, such as pulsed laser light, is emitted to the living body. Inside the living body to which the pulsed light has been emitted, the volume of the living tissue that has absorbed the energy of the pulsed light increases due to heat, and acoustic waves are generated. Therefore, it is possible to detect the acoustic waves using detection means, such as an ultrasound probe, and visualize the inside of the living body based on the electrical signal (photoacoustic signal) obtained by the detection.

Since the photoacoustic imaging apparatus forms an image based only on the acoustic waves emitted from a specific light absorber, the photoacoustic imaging apparatus is suitable for imaging a specific tissue in the living body, for example, a blood vessel.

On the other hand, as disclosed in, for example, JP2005-342128A and JP2006-055407A, an insertion operation for collecting tissues or injecting drugs using an insertion needle inserted into the living body has been known. When performing the insertion operation, it is required to be able to grasp the position of the insertion needle, especially, the distal end position by imaging it during the operation so that organs, tissues, and the like inside the living body are not damaged by the distal end of the insertion needle.

As a method of responding to the request, as conventionally disclosed in JP2005-342128A and JP2006-055407A, there has been known a method of displaying a part of a living body including an insertion needle on an ultrasound image so that the position of the insertion needle can be checked on the image. In such a method, however, there is a problem that, in a case where the insertion needle deviates from the scanning plane (scanning cross section) on which the insertion needle is being observed, it is difficult to check the insertion needle.

Therefore, JP2005-342128A proposes a method of generating an ultrasound image for a plurality of scanning cross sections and regarding a scanning cross section having the highest reflection brightness as a cross section through which the distal end of the insertion needle passes. JP2006-055407A proposes a method of determining the deviation of the insertion needle from the scanning cross section based on the difference between the amount of movement of the distal end of the insertion needle and the amount of movement of the insertion needle between the frames of an ultrasound image. JP2013-027513A discloses a method of displaying an insertion needle on a photoacoustic image so that the position of the insertion needle can be checked on the photoacoustic image.

SUMMARY OF THE INVENTION

However, in the generation of an ultrasound image, the reflection direction of the reflected ultrasound wave reflected at the distal end of the insertion needle changes according to the angle between the insertion needle and the ultrasound wave emitted to the insertion needle. For this reason, in the method disclosed in JP2005-342128A, depending on the angle at which ultrasound waves are reflected, everything having a high brightness is not necessarily a scanning cross section. Accordingly, the distal end position of the insertion needle may be erroneously detected.

In the method disclosed in JP2006-055407A, in a case where ultrasound waves do not hit the insertion needle vertically, the detection signal of the reflected ultrasound waves is weak. Accordingly, there is a problem that it is difficult to accurately calculate the amount of movement of the distal end of the insertion needle or the amount of movement of the insertion needle itself.

In the method disclosed in JP2013-027513A, since light emitted toward the insertion needle in the subject diffuses in the subject, the light emitted toward the insertion needle in the subject is emitted to the insertion needle or the like over a relatively wide range. Therefore, even if the distal end of the insertion needle is present at a position deviating from the scanning cross section, a photoacoustic image is drawn so that the distal end is present on the scanning cross section. As a result, the distal end position of the insertion needle may be erroneously detected.

The present invention has been made in view of the aforementioned situation, and it is an object of the present invention to provide a photoacoustic image generation method capable of accurately indicating whether or not the distal end of an interventional instrument, such as an insertion needle inserted into a subject, is present on the observation scanning plane generated as an image.

In addition, it is an object of the present invention to provide a photoacoustic image generation apparatus capable of implementing such a photoacoustic image generation method.

A photoacoustic image generation method according to the present invention is a photoacoustic image generation method for generating a photoacoustic image of a subject including an interventional instrument for each scanning plane. The photoacoustic image generation method includes: generating a reflected acoustic wave image of the subject for each scanning plane; generating a plurality of photoacoustic images and a plurality of reflected acoustic wave images for an observation scanning plane generated as an image; detecting a change in a photoacoustic image on the observation scanning plane from the plurality of photoacoustic images; detecting a change in a reflected acoustic wave image on the observation scanning plane from the plurality of reflected acoustic wave images; determining whether or not a distal end of the interventional instrument is present on the observation scanning plane based on the change in the photoacoustic image and the change in the reflected acoustic wave image; and sending notification of a result of the determination.

In the photoacoustic image generation method, for example, in a case where there are both the change in the photoacoustic image and the change in the reflected acoustic wave image, it may be determined that the distal end of the interventional instrument is present on the observation scanning plane. Here, it is assumed that "there are . . . changes" includes both a case where there are even small changes and a case where there are changes equal to or greater than a predetermined small value.

Alternatively, in a case where both the change in the photoacoustic image and the change in the reflected acoustic wave image are equal to or greater than a reference value set in advance, it may be determined that the distal end of the interventional instrument is present on the observation scanning plane.

It is preferable that the reference value described above is changeable.

In addition, it is preferable that the reference value described above is set for each of the change in the photoacoustic image and the change in the reflected acoustic wave image.

In the photoacoustic image generation method of the present invention, it is preferable that, in a case where a frame rate for generation of the photoacoustic image is different from a frame rate for generation of the reflected acoustic wave image, a change in a photoacoustic image is detected from two photoacoustic images that are most recent in generation order and a change in a reflected acoustic wave image is detected from two reflected acoustic wave images that are most recent in generation order.

On the other hand, a photoacoustic image generation apparatus according to the present invention is a photoacoustic image generation apparatus for generating a photoacoustic image of a subject including an interventional instrument for each scanning plane. The photoacoustic image generation apparatus comprises: means for generating a reflected acoustic wave image of the subject for each scanning plane; means for detecting a change in a photoacoustic image on an observation scanning plane, which is generated as an image, from a plurality of photoacoustic images regarding the observation scanning plane; means for detecting a change in a reflected acoustic wave image on the observation scanning plane from a plurality of reflected acoustic wave images regarding the observation scanning plane; determination means for determining whether or not a distal end of the interventional instrument is present on the observation scanning plane based on the change in the photoacoustic image and the change in the reflected acoustic wave image; and notification means for sending notification of a result of the determination.

It is preferable that, in a case where there are both the change in the photoacoustic image and the change in the reflected acoustic wave image, the determination means determines that the distal end of the interventional instrument is present on the observation scanning plane.

Alternatively, in a case where both the change in the photoacoustic image and the change in the reflected acoustic wave image are equal to or greater than a reference value set in advance, the determination means may determine that the distal end of the interventional instrument is present on the observation scanning plane.

It is preferable that the photoacoustic image generation apparatus of the present invention has means for changing the reference value described above.

In addition, it is preferable that the reference value described above is set for each of the change in the photoacoustic image and the change in the reflected acoustic wave image.

In the photoacoustic image generation apparatus of the present invention, it is preferable that means for detecting a change in the photoacoustic image detects a change in a photoacoustic image from two photoacoustic images that are most recent in generation order in a case where a frame rate for generation of a photoacoustic image is different from a frame rate for generation of a reflected acoustic wave image and that means for detecting a change in the reflected acoustic wave image detects a change in a photoacoustic image from two reflected acoustic wave images that are most recent in generation order in a case where the frame rate for generation of a photoacoustic image is different from the frame rate for generation of a reflected acoustic wave image.

According to the photoacoustic image generation method of the present invention, in the photoacoustic image generation method for generating a photoacoustic image of a subject including an interventional instrument for each scanning plane, a photoacoustic image and a reflected acoustic wave image of the subject including the interventional instrument are generated for each scanning plane, a plurality of photoacoustic images and a plurality of reflected acoustic wave images are generated for an observation scanning plane generated as an image, a change in a photoacoustic image on the observation scanning plane is detected from the plurality of photoacoustic images, a change in a reflected acoustic wave image on the observation scanning plane is detected from the plurality of reflected acoustic wave images, it is determined whether or not a distal end of the interventional instrument is present on the observation scanning plane based on the change in the photoacoustic image and the change in the reflected acoustic wave image, and notification of a result of the determination is sent. Therefore, it is possible to accurately determine whether or not the distal end of the interventional instrument is present on the observation scanning plane and to show the result to the operator of the insertion operation. Detailed reasons why it is possible to accurately determine whether or not the distal end of the interventional instrument is present on the observation scanning plane will be described in detail later according to the description of the following embodiments.

On the other hand, the photoacoustic image generation apparatus according to the present invention is a photoacoustic image generation apparatus for generating a photoacoustic image of a subject including an interventional instrument for each scanning plane. The photoacoustic image generation apparatus comprises: means for generating a reflected acoustic wave image of the subject for each scanning plane; means for detecting a change in a photoacoustic image on an observation scanning plane, which is generated as an image, from a plurality of photoacoustic images regarding the observation scanning plane; means for detecting a change in a reflected acoustic wave image on the observation scanning plane from a plurality of reflected acoustic wave images regarding the observation scanning plane; determination means for determining whether or not a distal end of the interventional instrument is present on the observation scanning plane based on the change in the photoacoustic image and the change in the reflected acoustic wave image; and notification means for sending notification of a result of the determination. Therefore, it is possible to implement the photoacoustic image generation method of the present invention described above.

DESCRIPTION OF THE PREFERRED EMBODIMENTS

Figure 1:
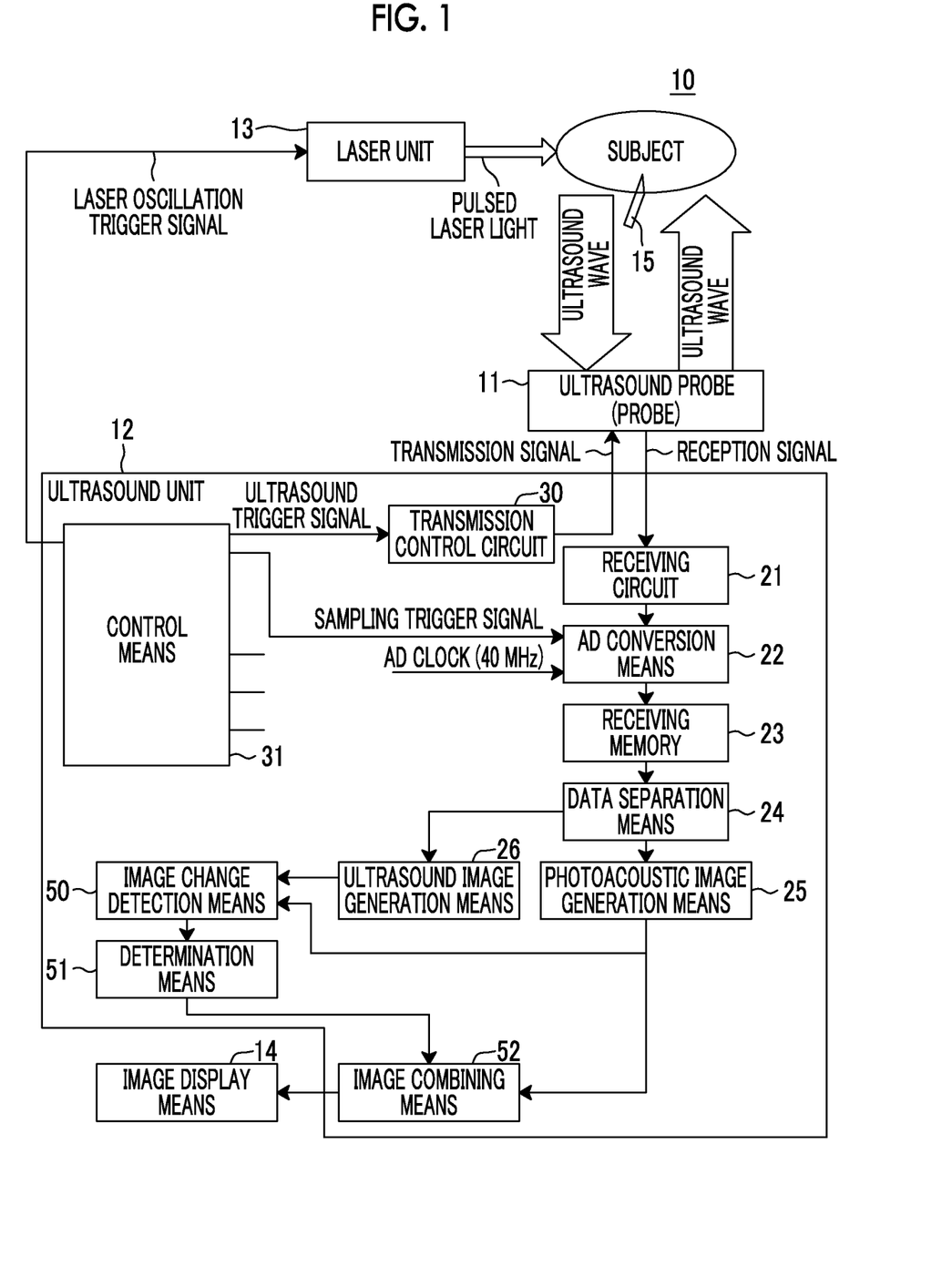
FIG. 1 is a block diagram showing the schematic configuration of a photoacoustic image generation apparatus according to a first embodiment of the present invention.

Hereinafter, embodiments of the present invention will be described in detail with reference to the diagrams. FIG. 1 is a block diagram showing the basic configuration of a photoacoustic image generation apparatus 10 according to a first embodiment of the present invention. The photoacoustic image generation apparatus 10 can generate both a photoacoustic image and an ultrasound image, and includes an ultrasound probe (probe) 11, an ultrasound unit 12, a laser unit 13, and image display means 14.

As the laser unit 13, for example, a laser unit that emits laser light having a center wavelength of 756 nm is applied. From the laser unit 13, pulsed laser light (hereinafter, simply referred to as laser light) is emitted toward a subject. Although the path of the laser light is schematically shown in FIG. 1, it is desirable that the laser light is guided to the probe 11 using guiding means, such as a plurality of optical fibers, and is emitted toward the subject from a portion of the probe 11.

The probe 11 performs output (transmission) of ultrasound waves to the subject and detection (reception) of reflected ultrasound waves that are reflected back from the subject. Therefore, the probe 11 has a plurality of ultrasound transducers arranged in a one-dimensional manner, for example. The probe 11 detects photoacoustic waves, which are generated when an observation part in the subject absorbs the laser light from the laser unit 13, with the plurality of ultrasound transducers. The probe 11 detects the photoacoustic waves and outputs a photoacoustic wave detection signal, and detects the reflected ultrasound waves (reflected acoustic waves) and outputs an ultrasound detection signal.

In a case where the guiding means described above is coupled to the probe 11, an end portion of the guiding means, that is, distal end portions of a plurality of optical fibers or the like are arranged along the arrangement direction of the plurality of ultrasound transducers. From the distal end portions, laser light is emitted toward the subject.

Hereinafter, the case where the guiding means is coupled to the probe 11 as described above will be described as an example.

When generating a photoacoustic image or an ultrasound image (reflected acoustic wave image) of the subject, the probe 11 is moved in a direction approximately perpendicular to the one-dimensional direction in which a plurality of ultrasound transducers are arranged. Accordingly, the subject is scanned in a two-dimensional manner with the laser light and the ultrasound waves. This scan may be performed by an examiner who manually moves the probe 11, or a more precise two-dimensional scan may be realized using a scanning mechanism.

Instead of the ultrasound waves described above, acoustic waves having audible frequencies may be used to generate an image based on the reflected acoustic waves.

The ultrasound unit 12 has a receiving circuit 21, AD conversion means 22, a receiving memory 23, data separation means 24, photoacoustic image generation means 25, ultrasound image generation means 26. The output of the photoacoustic image generation means 25 is input to the image display means 14, which is formed by using, for example, a CRT or a liquid crystal display device, through image combining means 52 to be described later. In addition, the ultrasound unit 12 has a transmission control circuit 30, control means 31 for controlling the operation of each section in the ultrasound unit 12, image change detection means 50, and determination means 51.

The receiving circuit 21 receives the photoacoustic wave detection signal and the ultrasound detection signal output from the probe 11. The AD conversion means 22 is sampling means, and samples the photoacoustic wave detection signal and the ultrasound detection signal received by the receiving circuit 21 and converts the photoacoustic wave detection signal and the ultrasound detection signal into photoacoustic data and ultrasound data that are digital signals. This sampling is performed at predetermined sampling periods in synchronization with an AD clock signal. The receiving circuit 21 may be configured to include the AD conversion means 22.

The laser unit 13 is configured to include a Ti: Sapphire laser, an optical parametric oscillation (OPO) laser based on the second harmonic excitation of a YAG laser, a Q-switch pulsed laser formed of an alexandrite laser, or the like. A laser oscillation trigger signal instructing the emission of light is input to the laser unit 13 from the control means 31. When the laser oscillation trigger signal is received, the laser unit 13 emits pulsed laser light having a wavelength of 756 nm. In addition, the laser unit 13 may be formed of other semiconductor lasers, for example.

The control means 31 inputs an ultrasound trigger signal instructing the transmission of ultrasound waves to the transmission control circuit 30. When the ultrasound trigger signal is received, the transmission control circuit 30 makes the probe 11 transmit ultrasound waves. The control means 31 outputs the laser oscillation trigger signal first, and then outputs the ultrasound trigger signal. Emission of laser light toward the subject in response to the output of the laser oscillation trigger signal and detection of photoacoustic waves are performed, and then transmission of ultrasound waves to the subject in response to the output of the ultrasound trigger signal and detection of reflected ultrasound waves are performed.

The control means 31 further outputs a sampling trigger signal instructing the start of sampling to the AD conversion means 22. The sampling trigger signal is output after the laser oscillation trigger signal is output and before the ultrasound trigger signal is output, more preferably, at a timing at which laser light is actually emitted toward the subject. Therefore, the sampling trigger signal is output in synchronization with a timing at which the control means 31 outputs the laser oscillation trigger signal, for example. In response to the reception of the sampling trigger signal, the AD conversion means 22 starts the sampling of the photoacoustic wave detection signal that is received by the receiving circuit 21 after being output from the probe 11.

The control means 31 outputs the ultrasound trigger signal at a timing, at which the detection of photoacoustic waves is ended, after outputting the laser oscillation trigger signal. At this time, the AD conversion means 22 continues the sampling without interrupting the sampling of a photoacoustic wave detection signal. In other words, the control means 31 outputs an ultrasound trigger signal in a state in which the AD conversion means 22 continues to sample the photoacoustic wave detection signal. In response to the ultrasound trigger signal, the probe 11 transmits ultrasound waves. Then, the detection target of the probe 11 is changed to reflected ultrasound waves from the photoacoustic waves. The AD conversion means 22 continuously samples the photoacoustic wave detection signal and the ultrasound detection signal by continuously sampling the detected ultrasound detection signal. The ultrasound trigger signal may be output after the AD conversion means 22 stops sampling the photoacoustic wave detection signal.

The AD conversion means 22 stores the photoacoustic data and the ultrasound data obtained by sampling in the common receiving memory 23. The sampling data stored in the receiving memory 23 is photoacoustic data up to a certain point in time, and is ultrasound data after the certain point in time. The data separation means 24 separates the photoacoustic data and the ultrasound data, which are stored in the receiving memory 23, from each other.

Hereinafter, generation and display of a photoacoustic image will be described. The ultrasound data and the photoacoustic data read from the receiving memory 23 are input to the data separation means 24 shown in FIG. 1. The data separation means 24 inputs only the photoacoustic data to the photoacoustic image generation means 25 at the subsequent stage when generating a photoacoustic image. The photoacoustic image generation means 25 generates a photoacoustic image relevant to a scanning plane (scanning cross section), which is scanned with laser light, based on the photoacoustic data, and inputs data indicating the photoacoustic image to the image display means 14 through the image combining means 52 to be described later. As a result, the photoacoustic image relevant to the scanning plane is displayed on the image display means 14. Here, the photoacoustic image is generated by processing including, for example, image reconstruction such as phase matching addition, detection, and logarithmic conversion.

The data separation means 24 inputs only the ultrasound data to the ultrasound image generation means 26 at the subsequent stage when generating an ultrasound image. The ultrasound image generation means 26 generates an ultrasound image relevant to the scanning plane, which is scanned with ultrasound waves, based on the ultrasound data. The ultrasound image is also generated by processing including, for example, image reconstruction such as phase matching addition, detection, and logarithmic conversion.

In the present embodiment, the photoacoustic image is generated to display the tissue, for example, blood vessels of the subject. However, the photoacoustic image may also be used so that the operator can check the position of an insertion needle 15 that is inserted into the subject, in particular, the distal end position of the insertion needle 15 by displaying the insertion needle 15. Then, in a case where it is determined that the distal end of the insertion needle 15 deviates from the scanning plane, a display showing a result of the determination is combined with the photoacoustic image by the image combining means 52, and the composite image is displayed on the image display means 14. On the other hand, in a case where it is determined that the distal end of the insertion needle 15 is present on the scanning plane, the above image combination is not performed, and data indicating the photoacoustic image is input to the image display means 14 through the image combining means 52. The above determination and display of a determination result will be described in detail later.

In addition, it is also possible to scan the subject in a two-dimensional manner with laser light by moving the probe 11 as described above and to generate and display a photoacoustic image, which shows a desired part of the subject, for example, blood vessels of the subject in a three-dimensional manner, based on image data regarding a plurality of cross sections obtained by the scanning.

Figure 2:
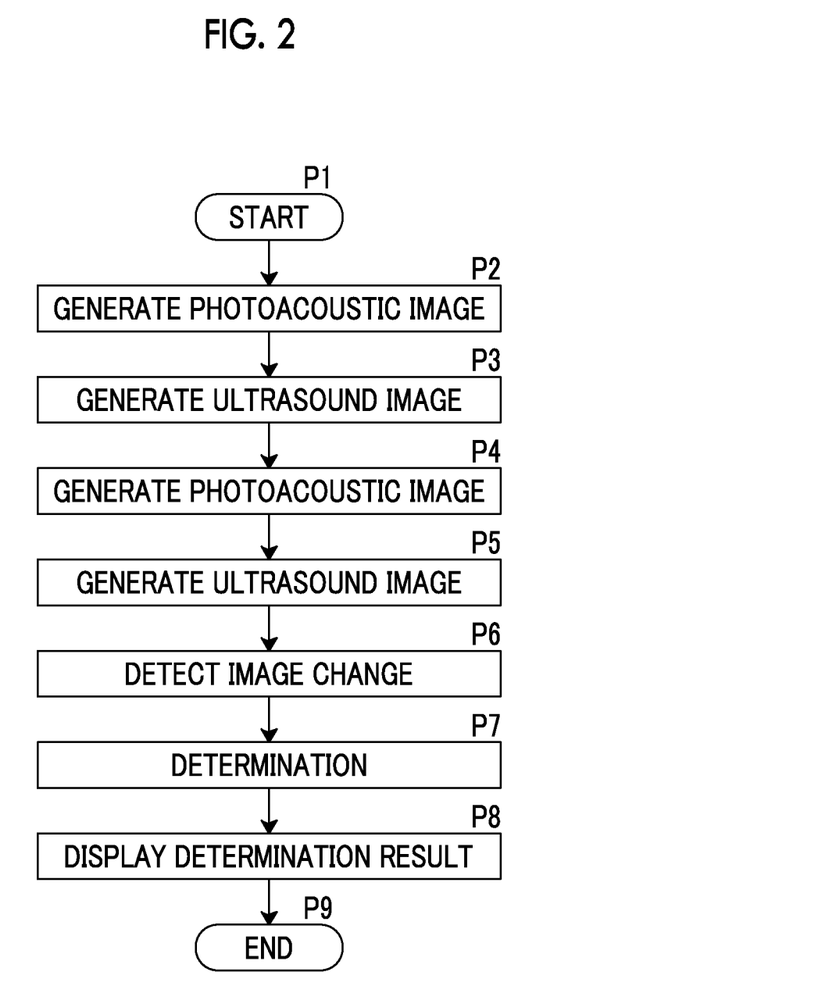
FIG. 2 is a flowchart showing a process for indicating the position of an insertion needle, which is performed by the apparatus shown in FIG. 1.
Figure 3:
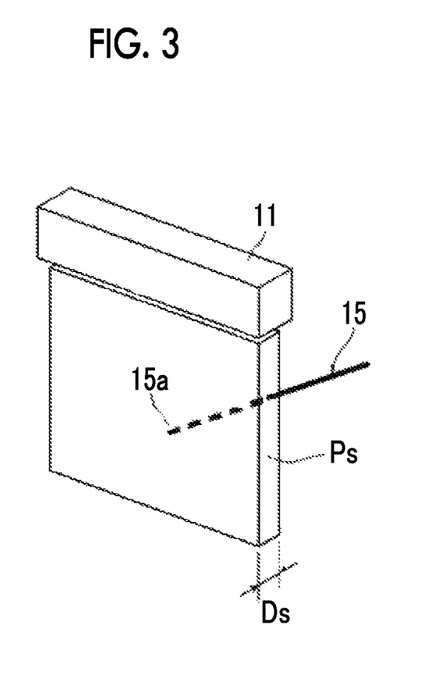
FIG. 3 is a schematic diagram showing an example of the relationship between an insertion needle and an observation scanning plane.
Figure 4:
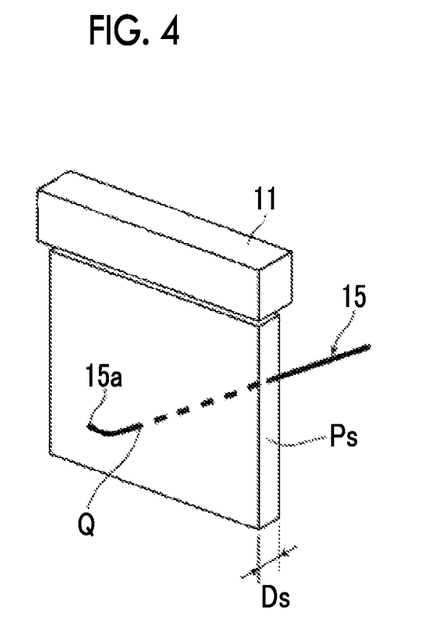
FIG. 4 is a schematic diagram showing another example of the relationship between the insertion needle and the observation scanning plane.

Next, a process of determining whether or not the distal end of the insertion needle 15 is present on the scanning plane will be described with reference to FIGS. 2 to 7. FIG. 2 shows the flow of a process controlled by, for example, the control means 31 shown in FIG. 1 in order to perform this determination. FIGS. 3 and 4 schematically show the relationship between a scanning plane (scanning cross section) Ps and the insertion needle 15. The scanning plane Ps is a surface that is obtained by generating an image and is provided for observation. Hereinafter, the scanning plane Ps is referred to as the observation scanning plane Ps.

Ultrasound waves emitted from a plurality of ultrasound transducers arranged in the one-dimensional manner in the probe 11 are emitted to the subject with a certain width after being narrowed down by an acoustic lens or the like. In addition, detection of reflected ultrasound waves is also performed by an ultrasound transducer having a certain width. Therefore, one observation scanning plane Ps indicates information on a cross section having a certain width Ds (slice width). Accordingly, in a case where the insertion needle 15 is present within the width Ds, a photoacoustic image or an ultrasound image is drawn so that the insertion needle 15 is present on the observation scanning plane Ps.

In the example shown in FIG. 3, as the imaging range of the insertion needle 15, the entire portion including a distal end 15a falls within the observation scanning plane Ps. When performing an insertion operation, such as tissue collection or drug injection using the insertion needle 15, the insertion needle 15 is pushed in the lower left direction in FIG. 3, that is, in a direction to advance the distal end 15a forward. In such a case, as in the example shown in FIG. 4, a distal end portion including the distal end 15a of the insertion needle 15 may deviate from the observation scanning plane Ps.

Figure 5:
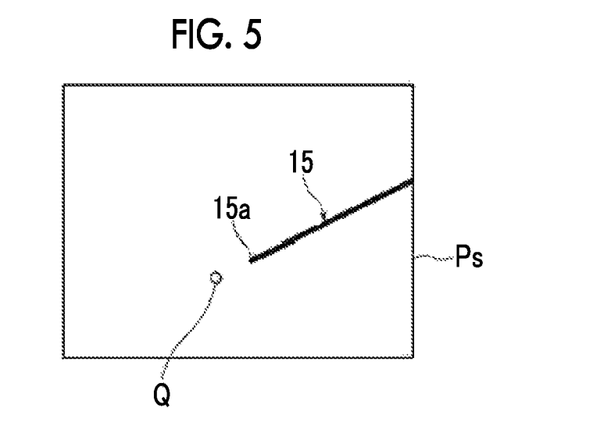
FIG. 5 is a schematic diagram showing a display example of the insertion needle in a photoacoustic image and an ultrasound image.

FIGS. 5 to 7 explain how the insertion needle 15 is shown in a photoacoustic image and an ultrasound image when the relationship between the insertion needle 15 and the observation scanning plane Ps is in a state shown in FIG. 3 or 4. In the case of the state shown in FIG. 3, as shown in FIG. 5, both the photoacoustic image and the ultrasound image are drawn so that a portion including the distal end 15a of the insertion needle 15 is present on the observation scanning plane Ps. In FIG. 5, a position to which the insertion needle 15 deviates from the observation scanning plane Ps as will be described later is shown by Q.

Figure 6:
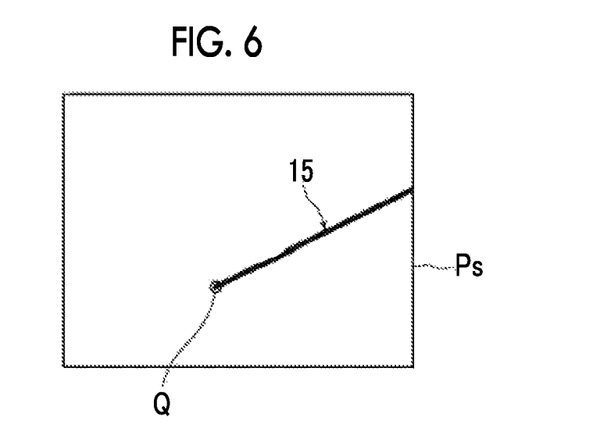
FIG. 6 is a schematic diagram showing a display example of the insertion needle in an ultrasound image.
Figure 7:
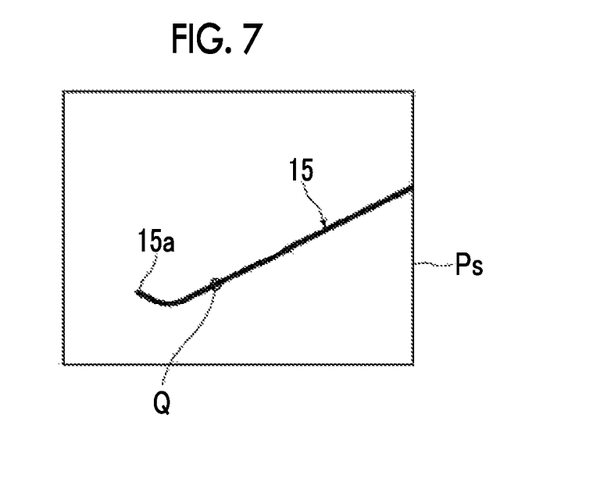
FIG. 7 is a schematic diagram showing a display example of the insertion needle in a photoacoustic image.

In the case of the state shown in FIG. 4, in the ultrasound image, the insertion needle 15 is drawn so that only the portion of the range included in the observation scanning plane Ps is drawn, as shown in FIG. 6. In contrast, in the photoacoustic image, as shown in FIG. 7, the insertion needle 15 may be drawn including a distal end portion (the distal end 15a and a portion in the vicinity thereof) present at a position deviating from the observation scanning plane Ps. That is, in the generation of a photoacoustic image, since the laser light emitted toward the subject expands due to diffusion or the like, the emission range becomes wider than that of the ultrasound wave when generating the ultrasound image. Then, the laser light is also emitted to the distal end portion of the insertion needle 15 present at the position deviating from the observation scanning plane Ps. Accordingly, photoacoustic waves generated from the distal end portion are detected by the probe 11. As a result, a photoacoustic image in which the distal end portion of the insertion needle 15 is present on the observation scanning plane Ps is generated. When laser light is received, stronger photoacoustic waves are generated from the distal end portion of the insertion needle 15 normally formed of metal, compared with the tissue or the like of the subject. For this reason, the distal end portion is particularly easy to be imaged.

Alternatively, as another example of strengthening photoacoustic waves from the distal end portion of the insertion needle 15, it is also possible to generate photoacoustic waves by introducing light into the insertion needle using an optical fiber or the like and emitting the light directly to the distal end portion, the tissue of the distal end portion, or a light absorption member of the distal end portion to be described later. As still another example, a member for generating sound waves can be attached to the distal end portion of the insertion needle 15, so that sound waves can be generated from the distal end portion without using light.

If the operator of the insertion operation grasps the distal end portion of the insertion needle 15 by observing such a photoacoustic image, organs, tissues, and the like including blood vessels at the tip of the insertion needle 15 are not recognized. Accordingly, it may be determined that there is no problem even if the insertion needle 15 is further pushed. In addition, at a portion close to the distal end 15a of the insertion needle 15, it is desirable that a light absorption member for promoting the generation of acoustic waves by increasing the absorption efficiency of laser light is disposed by means of embedding, coating, or the like. As such a light absorption member, for example, black fluororesin can be mentioned.

In the present embodiment, such a situation can be prevented by performing the process whose flow is shown in FIG. 2. Hereinafter, the process shown in FIG. 2 will be described. This process starts in step P1. Then, in steps P2, P3, P4, and P5, generation of a photoacoustic image, generation of an ultrasound image, generation of a photoacoustic image, and generation of an ultrasound image are performed, respectively, for one common observation scanning plane Ps. Data indicating a plurality of photoacoustic images and a plurality of ultrasound images obtained in this manner is temporarily stored in, for example, storage means provided in the control means 31 shown in FIG. 1.

Each of the generation of a photoacoustic image and the generation of an ultrasound image may be performed multiple times, and the number of times or the order of generation of each image is not limited those described above. For example, a process of performing the generation of a photoacoustic image three times in succession and then performing the generation of an ultrasound image once may be repeated multiple times.

Then, in step P6, the image change detection means 50 detects a change in the photoacoustic image and a change in the ultrasound image on the observation scanning plane Ps based on the data read from the storage means. The detection of the image change is made by calculating a change between two photoacoustic images that are most recent in generation order, or similarly, between two ultrasound images that are most recent in generation order. Even in a case where the frame rates for generating both images are different, such as the case of performing the generation of a photoacoustic image three times in succession and then performing the generation of an ultrasound image once as described above, it is desirable to calculate a change between two photoacoustic images that are most recent in generation order, or similarly, between two ultrasound images that are most recent in generation order.

Specifically, the calculation of an image change can be performed using commonly known methods, such as finding the correlation of images between frames using block matching, template matching, or the like. In addition, the amount of change in an image due to pulsation before the insertion of the insertion needle 15 may be calculated in advance so that the change in an image due to the insertion of the insertion needle 15 and the change in an image due to the pulsation of the subject can be distinguished, and the amount of change in an image due to pulsation may be subtracted from the amount of change in an image after the insertion of the insertion needle 15. Alternatively, if it is known that the change in an image due to pulsation occurs from the movement of the subject in a certain fixed direction, the amount of change in the image may be calculated in consideration of the movement in the direction, thereby avoiding the influence of pulsation on the change in the image.

Then, in step P7, based on the change in the photoacoustic image and the change in the ultrasound image calculated as described above, the determination means 51 determines whether or not the distal end 15a of the insertion needle 15 is present on the observation scanning plane Ps. In a case where changes have been detected in both the photoacoustic image and the ultrasound image, it is determined that the distal end 15a of the insertion needle 15 is present on the observation scanning plane Ps. Otherwise, it is determined that the distal end 15a of the insertion needle 15 is not present on the observation scanning plane Ps.

That is, in a case where the relationship between the insertion needle 15 and the observation scanning plane Ps is a state shown in FIG. 3, both the ultrasound image and the photoacoustic image are drawn as shown in FIG. 5 as described above. Therefore, if the insertion needle 15 is moved by being pushed toward the distal end 15a, changes occur in both the ultrasound image and the photoacoustic image. In contrast, in a case where the relationship between the insertion needle 15 and the observation scanning plane Ps is a state shown in FIG. 4, the photoacoustic image is drawn as shown in FIG. 7 as described above, a change occurs in the photoacoustic image according to the movement of the insertion needle 15 including the distal end 15a. However, in the ultrasound image in which the distal end portion is not displayed as shown in FIG. 6, even if the insertion needle 15 moves, only the drawn portion is changed. Accordingly, there is no change in the image.

Considering the influence of the movement of the tissue due to pulsation, if the amount of change in the image is a change within a predetermined value due to pulsation, this may be assumed that there is no change in the image. In addition, in a case where the amount of change in the image due to pulsation is subtracted from the amount of change in the image after the insertion of the insertion needle 15, it can be determined that the amount of change in the image after the subtraction total is due only to the movement of the insertion needle 15. Here, the predetermined value may be the same value for the photoacoustic image and the ultrasound image, or may be different for the photoacoustic image and the ultrasound image.

Then, in step P8, the result of the determination is displayed. Information indicating the determination result is input to the image combining means 52, a display based on the information is combined with the photoacoustic image, and the composite image is displayed on the image display means 14. The series of processes described above are ended in the next step P9. The above display in the present embodiment shows whether or not the distal end 15a of the insertion needle 15 is present on the observation scanning plane Ps, for example. However, only when the distal end 15a of the insertion needle 15 deviates from the observation scanning plane Ps, a display showing the situation may be output. As described above, in the present embodiment, notification means is formed by the image combining means 52 and the image display means 14.

A warning sound may be emitted at the same time as when outputting a display showing that the distal end 15a of the insertion needle 15 deviates from the observation scanning plane Ps, or only the warning sound may be emitted without outputting the display.

Figure 8:
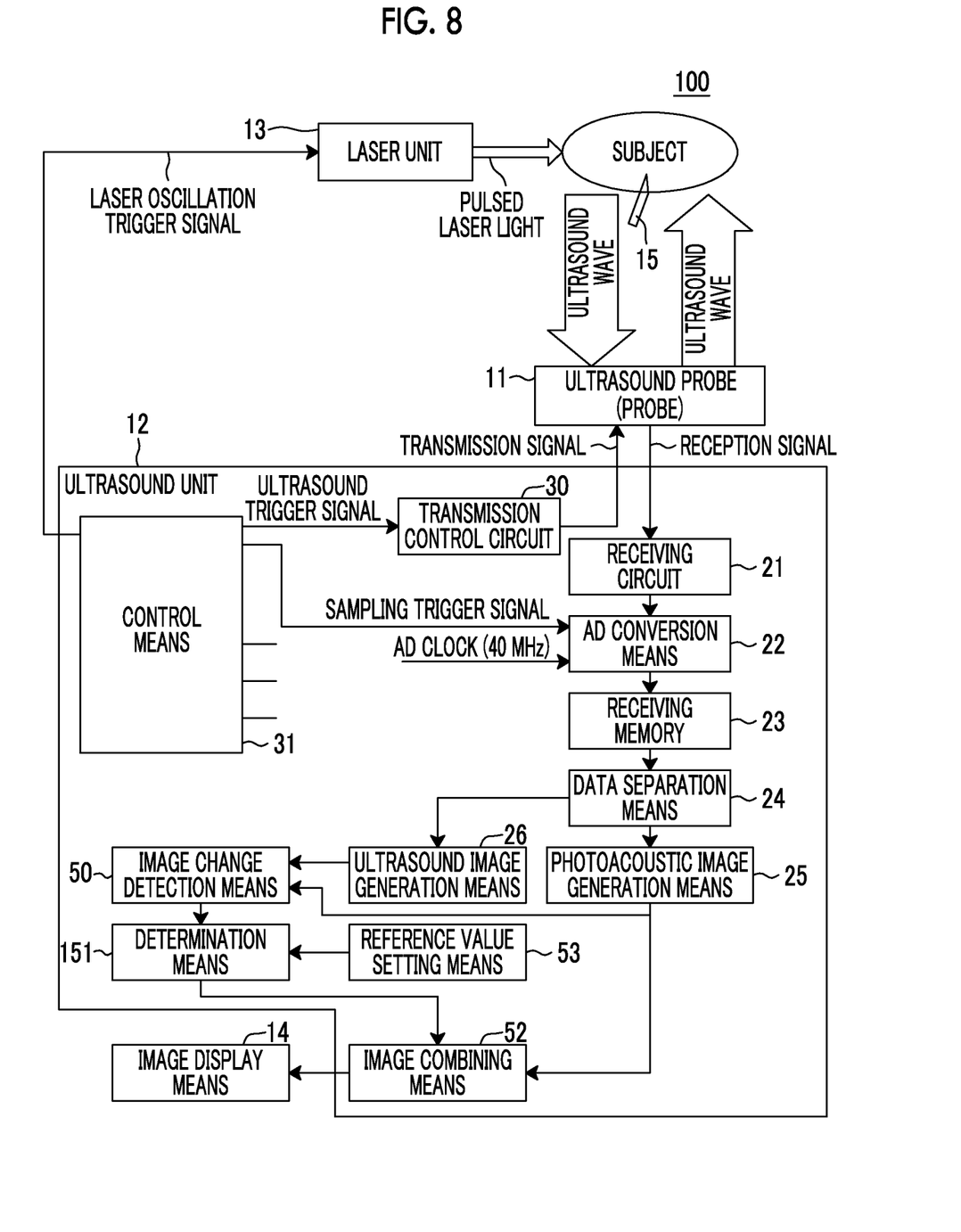
FIG. 8 is a block diagram showing the schematic configuration of a photoacoustic image generation apparatus according to a second embodiment of the present invention.

Next, a second embodiment of the present invention will be described with reference to FIG. 8. FIG. 8 is a block diagram showing the basic configuration of a photoacoustic image generation apparatus 100 according to the second embodiment of the present invention. In FIG. 8, the same elements as in FIG. 1 described previously are denoted by the same reference numerals, and the explanation thereof will be omitted unless particularly required. The photoacoustic image generation apparatus 100 is basically different from the photoacoustic image generation apparatus 10 shown in FIG. 1 in that the configuration of determination means 151 is different from the determination means 51 and reference value setting means 53 is added.

The reference value setting means 53 sets an assumed reference value for the amount of change in an image, and information indicating the reference value is input to the determination means 151. The determination means 151 compares each of the change in the photoacoustic image and the change in the ultrasound image on the observation scanning plane Ps, which have been calculated by the image change detection means 50, with the reference value, and determines that the distal end 15a of the insertion needle 15 is present on the observation scanning plane Ps in a case where the changes in both the images are equal to or greater than the reference value. Otherwise, it is determined that the distal end 15a of the insertion needle 15 is not present on the observation scanning plane Ps. Then, the notification of the determination result using display or warning sound is the same as in the first embodiment.

The reference value may be the same value for the photoacoustic image and the ultrasound image, or may be different for the photoacoustic image and the ultrasound image. It is desirable to set the reference value so as to be changeable.

While the embodiment in a case where an interventional instrument is the insertion needle 15 has been described, the present invention can be similarly applied to a case where an interventional instrument inserted into the subject is not an insertion needle. Also in this case, the same effect as the effect described above is obtained. An interventional instrument other than the insertion needle may be, for example, a catheter inserted into a blood vessel, or may be a guide wire of a catheter inserted into a blood vessel. In addition, an interventional instrument may be a needle for radiofrequency cautery in which an electrode used in radiofrequency cautery is housed, or may be an optical fiber for laser treatment.

In addition, not only can the generated ultrasound image be used to determine whether or not the distal end 15a of the insertion needle 15 is present on the observation scanning plane Ps, but also the generated ultrasound image can be displayed on the image display means 14 solely or in combination with the photoacoustic image in order to show the observation scanning plane Ps of the subject.

What is claimed is:

1. A photoacoustic image generation method for generating a photoacoustic image of a subject including an interventional instrument for each scanning plane, the method comprising:
    generating a reflected acoustic wave image of the subject for each scanning plane;
    generating a plurality of photoacoustic images and a plurality of reflected acoustic wave images for an observation scanning plane generated as an image;
    detecting a first change in a photoacoustic image on the observation scanning plane from the plurality of photoacoustic images;
    detecting a second change in a reflected acoustic wave image on the observation scanning plane from the plurality of reflected acoustic wave images;
    determining whether or not a distal end of the interventional instrument is present on the observation scanning plane based on the first change in the photoacoustic image and the second change in the reflected acoustic wave image; and
    sending notification of a result of the determination.

2. The photoacoustic image generation method according to claim 1,
    wherein, in a case where there are both the first change in the photoacoustic image and the second change in the reflected acoustic wave image, it is determined that the distal end of the interventional instrument is present on the observation scanning plane.

3. The photoacoustic image generation method according to claim 2,
    wherein, in a case where a frame rate for generation of the plurality of photoacoustic images is different from a frame rate for generation of the plurality of reflected acoustic wave images, the first change in a photoacoustic image is detected from two photoacoustic images that are most recent in generation order and the second change in a reflected acoustic wave image is detected from two reflected acoustic wave images that are most recent in generation order.

4. The photoacoustic image generation method according to claim 1,
    wherein, in a case where both the first change in the photoacoustic image and the second change in the reflected acoustic wave image are equal to or greater than a reference value set in advance, it is determined that the distal end of the interventional instrument is present on the observation scanning plane.

5. The photoacoustic image generation method according to claim 4,
wherein the reference value is changeable.

6. The photoacoustic image generation method according to claim 5,
wherein the reference value is set for each of the first change in the photoacoustic image and the second change in the reflected acoustic wave image.

7. The photoacoustic image generation method according to claim 5,
wherein, in a case where a frame rate for generation of the plurality of photoacoustic images is different from a frame rate for generation of the plurality of reflected acoustic wave images, the first change in a photoacoustic image is detected from two photoacoustic images that are most recent in generation order and the second change in a reflected acoustic wave image is detected from two reflected acoustic wave images that are most recent in generation order.

8. The photoacoustic image generation method according to claim 4,
wherein the reference value is set for each of the first change in the photoacoustic image and the second change in the reflected acoustic wave image.

9. The photoacoustic image generation method according to claim 4,
wherein, in a case where a frame rate for generation of the plurality of photoacoustic images is different from a frame rate for generation of the plurality of reflected acoustic wave images, the first change in a photoacoustic image is detected from two photoacoustic images that are most recent in generation order and the second change in a reflected acoustic wave image is detected from two reflected acoustic wave images that are most recent in generation order.

10. The photoacoustic image generation method according to claim 1,
wherein, in a case where a frame rate for generation of the plurality of photoacoustic images is different from a frame rate for generation of the plurality of reflected acoustic wave images, the first change in a photoacoustic image is detected from two photoacoustic images that are most recent in generation order and the second change in a reflected acoustic wave image is detected from two reflected acoustic wave images that are most recent in generation order.

* * * * *